(12) United States Patent
Bitter et al.

(10) Patent No.: US 9,030,666 B2
(45) Date of Patent: May 12, 2015

(54) NON-DISPERSIVE GAS ANALYZER

(75) Inventors: Ralf Bitter, Karlsruhe (DE); Camiel Heffels, Stutensee-Büchig (DE); Thomas Hörner, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 67 days.

(21) Appl. No.: 13/805,225

(22) PCT Filed: Jun. 22, 2011

(86) PCT No.: PCT/EP2011/060402
§ 371 (c)(1),
(2), (4) Date: Apr. 9, 2013

(87) PCT Pub. No.: WO2011/161137
PCT Pub. Date: Dec. 29, 2011

(65) Prior Publication Data
US 2013/0208280 A1    Aug. 15, 2013

(30) Foreign Application Priority Data
Jun. 25, 2010 (DE) .......................... 10 2010 030 549

(51) Int. Cl.
*G01N 21/61* (2006.01)
*G01N 21/27* (2006.01)
(Continued)

(52) U.S. Cl.
CPC ............... *G01N 21/61* (2013.01); *G01N 21/05* (2013.01); *G01N 21/274* (2013.01); *G01N 21/31* (2013.01); *G01N 21/33* (2013.01); *G01N 21/3504* (2013.01); *G01N 2021/3155* (2013.01); *G01N 2201/0696* (2013.01)

(58) Field of Classification Search
USPC ......... 356/432–437, 246, 51; 250/344, 338.1, 250/330–335, 339.01–339.16, 340
See application file for complete search history.

(56) References Cited

U.S. PATENT DOCUMENTS

| 3,810,696 | A |   | 5/1974 | Hutchins, Jr. |
| 4,271,124 | A | * | 6/1981 | Speeter ..................... 422/82.09 |

(Continued)

FOREIGN PATENT DOCUMENTS

| DE | 2408197 A1 | 8/1974 |
| DE | 3902015 C2 | 7/1991 |

(Continued)

OTHER PUBLICATIONS

J. Staab: "Industrielle Gasanalyse", R. Oldenbourg Verlag München Wien, 1994, Seiten 83, 133.

(Continued)

*Primary Examiner* — Sang Nguyen
(74) *Attorney, Agent, or Firm* — Cozen O'Connor

(57) ABSTRACT

A non-dispersive gas analyzer comprising a light source, having light that shines through a measuring cuvette containing a measuring gas to be analyzed onto a non selective detector having a downstream evaluation unit, wherein a multi-component gas analysis is made possible using in a simple manner in that the light source is a flash discharge lamp and the evaluation unit is configured to evaluate the temporal pulse curves of the flash shining onto the detector such that it is possible to take advantage of the property of flash discharge lamps in that the emitted wavelength components vary over the duration of the flash.

9 Claims, 5 Drawing Sheets

(51) Int. Cl.
    *G01N 21/31*     (2006.01)
    *G01N 21/3504*     (2014.01)
    *G01N 21/05*     (2006.01)
    *G01N 21/33*     (2006.01)

(56) References Cited

U.S. PATENT DOCUMENTS

| | | | |
|---|---|---|---|
| 4,320,297 A * | 3/1982 | Cederstrand et al. | 250/343 |
| 4,355,233 A * | 10/1982 | Warnke et al. | 250/343 |
| 4,420,687 A * | 12/1983 | Martinez et al. | 250/343 |
| 4,687,329 A | 8/1987 | Schultz | |
| 4,692,621 A * | 9/1987 | Passaro et al. | 250/343 |
| 4,899,053 A | 2/1990 | Lai et al. | |
| 4,986,654 A | 1/1991 | Meijer et al. | |
| 5,080,767 A * | 1/1992 | Ando et al. | 204/158.1 |
| 5,130,776 A | 7/1992 | Popovic et al. | |
| 5,429,805 A * | 7/1995 | Uno et al. | 422/83 |
| 5,734,165 A | 3/1998 | Unal et al. | |
| 5,807,750 A * | 9/1998 | Baum et al. | 436/164 |
| 5,886,348 A * | 3/1999 | Lessure et al. | 250/339.13 |
| 6,074,607 A | 6/2000 | Slovacek et al. | |
| 6,166,383 A * | 12/2000 | Kimmig et al. | 250/343 |
| 6,794,670 B1 | 9/2004 | Folestad et al. | |
| 7,063,667 B1 | 6/2006 | Ben-Oren et al. | |
| 7,180,595 B2 * | 2/2007 | Willing et al. | 356/437 |
| 7,755,767 B2 | 7/2010 | Ruth et al. | |
| 8,044,353 B2 | 10/2011 | Bitter et al. | |
| 2001/0032514 A1 * | 10/2001 | Maruyama | 73/657 |
| 2002/0101592 A1 | 8/2002 | Zare et al. | |
| 2005/0082483 A1 * | 4/2005 | Oida et al. | 250/343 |
| 2005/0157303 A1 | 7/2005 | Langford et al. | |
| 2006/0181710 A1 | 8/2006 | Kachanov et al. | |
| 2007/0216903 A1 | 9/2007 | Cole et al. | |
| 2009/0124918 A1 | 5/2009 | Stockmann et al. | |
| 2009/0146080 A1 | 6/2009 | Liebsch | |
| 2012/0205547 A1 * | 8/2012 | Klinkhammer et al. | 250/373 |

FOREIGN PATENT DOCUMENTS

| | | |
|---|---|---|
| DE | 3887528 T2 | 8/1994 |
| DE | 4403763 A1 | 8/1995 |
| DE | 4440968 A1 | 5/1996 |
| DE | 19608907 C1 | 4/1997 |
| DE | 69729632 T2 | 7/2005 |
| DE | 69828799 T2 | 1/2006 |
| DE | 102005036410 A1 | 2/2007 |
| DE | 102008044317 A1 | 6/2010 |
| EP | 0283047 A2 | 9/1988 |
| EP | 0387483 A1 | 9/1990 |
| EP | 0195339 B1 | 7/1992 |
| EP | 0591758 A1 | 4/1994 |
| EP | 0758079 A2 | 2/1997 |
| GB | 2358245 A | 7/2001 |
| WO | WO 9914576 A2 | 3/1999 |
| WO | WO 2004048907 A2 | 6/2004 |
| WO | WO 2007107366 A1 | 9/2007 |
| WO | WO 2009101197 A1 | 8/2009 |

OTHER PUBLICATIONS

File: Rare gas flashtube spectral outputs.JPG; http://en.wikipedia.org/wiki/File:Rare_gas_flashtube_spectral_outputs.jpg Jun. 15, 2010 (3 pages).

Oriel Xenon Flashlamp System, Light Sources http://support.newport.com/file_store/PDFs/tempPDFs/e5457_Oriel-Xenon-Flashlamp-Systems.pdf Jun. 15, 2010 (3 pages).

* cited by examiner

NON-DISPERSIVE GAS ANALYZER

CROSS-REFERENCE TO RELATED APPLICATIONS

This is a U.S. national stage of application No. PCT/EP2011/060402 filed 22 Jun. 2011. Priority is claimed on German Application No. 10 2010 030 549.9 filed 25 Jun. 2010, the content of which is incorporated herein by reference in its entirety.

BACKGROUND OF THE INVENTION

1. Field of the Invention

The invention relates to a non-dispersive gas analyzer having a light source, whose light is incident through a measuring cuvette, which contains a measured gas to be analyzed, on a non-selective detector having analysis device connected downstream.

2. Description of the Related Art

In absorption-spectrometric gas analysis, predefined components of a gas mixture (measured gas) are quantitatively determined based on their wavelength-specific absorption of light. For this purpose, the light of a light source is guided through the measured gas to be analyzed onto a detector having an analysis device connected downstream. To obtain a defined absorption path, the measured gas is typically contained in a measuring cuvette. The wavelength range of the light that is used is oriented according to the components of the measured gas to be determined and can extend from the near infrared to the ultraviolet or can lie in-between. In non-dispersive gas analysis, there is no spectral decomposition of the light. Instead, selective, optionally tunable, light sources or selective detectors are used. For example, a non-dispersive infrared (NDIR) gas analyzer typically contains a non-selective infrared radiation source and a selective optopneumatic detector that is filled with the component or components to be determined. In another example, a laser spectrometer contains a selective light source in the form of a wavelength-tunable laser and a detector that is non-selective in the observed wavelength range, e.g., a photodiode. In so-called two-beam devices, the light of the light source is portioned onto the measuring cuvette and a reference cuvette filled with a non absorbing reference or zero gas having a downstream further detector and the differential signal of both detectors is analyzed in the analysis device (J. Staab: "Industrielle Gasanalyse [Industrial Gas Analysis]" R. Oldenbourg Verlag Munich Vienna, 1994, page 83).

The light is typically modulated to obtain an alternating signal in the detector. For this purpose, the light beam can be periodically interrupted using a vane wheel or aperture wheel or the light source can be activated in a pulsed manner.

The use of flash discharge lamps in gas analyzers, in particular xenon flash lamps, which have a broadband emission spectrum from ultraviolet to the near infrared, is known (see, e.g., J. Staab: "Industrielle Gasanalyse [Industrial Gas Analysis]" R. Oldenbourg Verlag Munich Vienna, 1994, page 133).

Thus, EP 0 591 758 A1 and EP 0 195 339 B1 each disclose a dispersive gas analyzer having a xenon flash lamp. The light is spectrally decomposed by an optical grating after being transmitted through the measuring cuvette and directed to a detector line made of photodiodes, for example.

It is known that the light flash generated by a flash discharge lamp has a differing time behavior with respect to the emitted wavelengths. Thus, the duration of the light flash of a xenon flash lamp is shortest in the ultraviolet range and longest in the infrared range (see, e.g., Newport Corporation, Oriel xenon flash lamps, Technical Information, found on Jun. 15, 2010 in the Internet under: http://support.newport.com/file$_{13}$store/PDFs/tempPDFs/e5457_Oriel-Xenon-Flashlamp-Systems.pdf).

SUMMARY OF THE INVENTION

It is therefore an object of the invention to provide a device for performing a gas analysis, in particular multicomponent gas analysis, in a simple manner.

This and other objects and advantages are achieved in accordance with the invention in which the light source of a non-dispersive gas analyzer is a flash discharge lamp, and the analysis device is configured to analyze the time pulse curve of the light flash incident on the detector.

The invention advantageously makes use of the above-mentioned property of flash discharge lamps, i.e., the emitted wavelength components vary over the duration of the light flash. Therefore, light absorptions occurring at different wavelengths in the measured gas to be analyzed can be determined via the time pulse curve of the light flash incident on the detector.

Depending on the components of the measured gas to be determined, the flash discharge lamp can contain different gas fillings. Flash light spectra of flash discharge lamps having different noble gas fillings are found in the Internet under: http://en.wikipedia.org/wiki/Flashtube. A commercially available xenon flash lamp is preferably used.

Those detectors that are sufficiently sensitive for the respective observed wavelength range and using which the time resolution in the microsecond range is achieved, which is required for the analysis of the time pulse curve of the light flash incident on the detector, come into consideration as the detector. Preferred detectors are photodiodes and photocells. In very broadband detectors, suitable optical bandpass filters (interference filters) can be placed in front of them, which mask out interfering wavelength ranges outside the observed wavelength range.

To analyze the time pulse curve, the analysis device can be configured to analyze the frequency content of the pulse shape. In principle, the analysis of the pulse curve can be performed in the time range and frequency range. The analysis can thus also relate to time components. In addition to the complex multivariate analysis of time components, this also includes very simple, partially empirical methods, such as the analysis of the time shift of the pulse peak, differentiation of the pulse curve (i.e., gradient analysis, curve discussions), integrations (area analyses), etc.

In a multicomponent measured gas, the pulse components that are missing, because they are absorbed or scattered by the components of the measured gas, can be determined in the analysis device by multivariate models from the time pulse curve of the light flash incident on the detector. The concentrations of the individual components in the measured gas can be determined comparably with the chemometric analysis of spectra. The further apart the absorption bands of the gases of the components to be measured, which are to be differentiated in their location, lie spectrally and the more strongly these bands are pronounced, the greater the gas-specific pulse forming influences and the better the separation via the methods described here. In this manner, for example, the concentration of $SO_2$, $O_3$, $H_2S$, and $NO_2$ could be quantitatively determined.

To reference the measurement and make it independent of reproducibility variations of the light flashes and longer drift appearances, e.g., aging of the light source and the detector, a reference cuvette, which is filled with a reference or zero gas, having a further detector arranged downstream is preferably provided, where a light distributor portions the light emitted by the light source onto the measuring cuvette and the reference cuvette and the analysis device is configured to analyze the differential pulse curve of the light flashes incident on the detectors.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For the further explanation of the invention, reference is made hereafter to the figures of the drawing; in the individual figures, which are each in the form of an exemplary embodiment, in which.

DETAILED DESCRIPTION OF THE PREFERRED EMBODIMENTS

Figure 1:
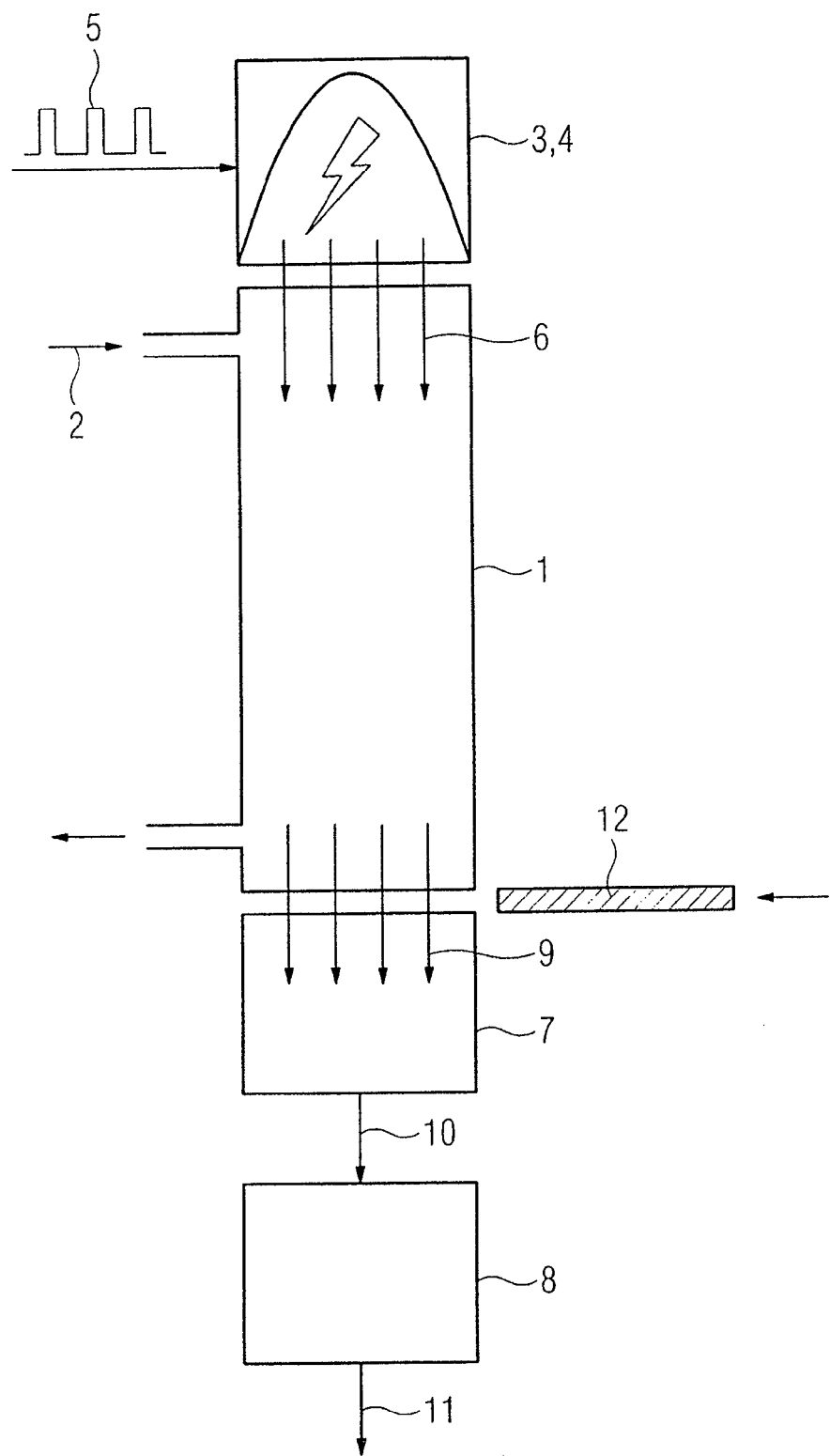
FIG. 1 shows a one-beam gas analyzer in accordance with the invention.

FIG. 1 shows a schematic illustration of a non-dispersive gas analyzer in a one-beam embodiment having a measuring cuvette 1, through which a measured gas 2 to be analyzed flows. The measured gas 2 is a gas mixture made up of multiple components, of which one or more components of interest are to be quantitatively determined. A light source 3 in the form of a flash discharge lamp 4, for example, a xenon flash lamp, is activated by electrical pulses 5 and generates individual light flashes 6, which are conducted through the measuring cuvette 1 onto a detector 7. An analysis device 8 is connected downstream from the detector 7, which analyzes the pulsed detector signal 10, which is generated by the detector 7 as a reaction to the respective received light flash 9, with respect to the pulse shape and delivers an analysis result 11.

Figure 2:
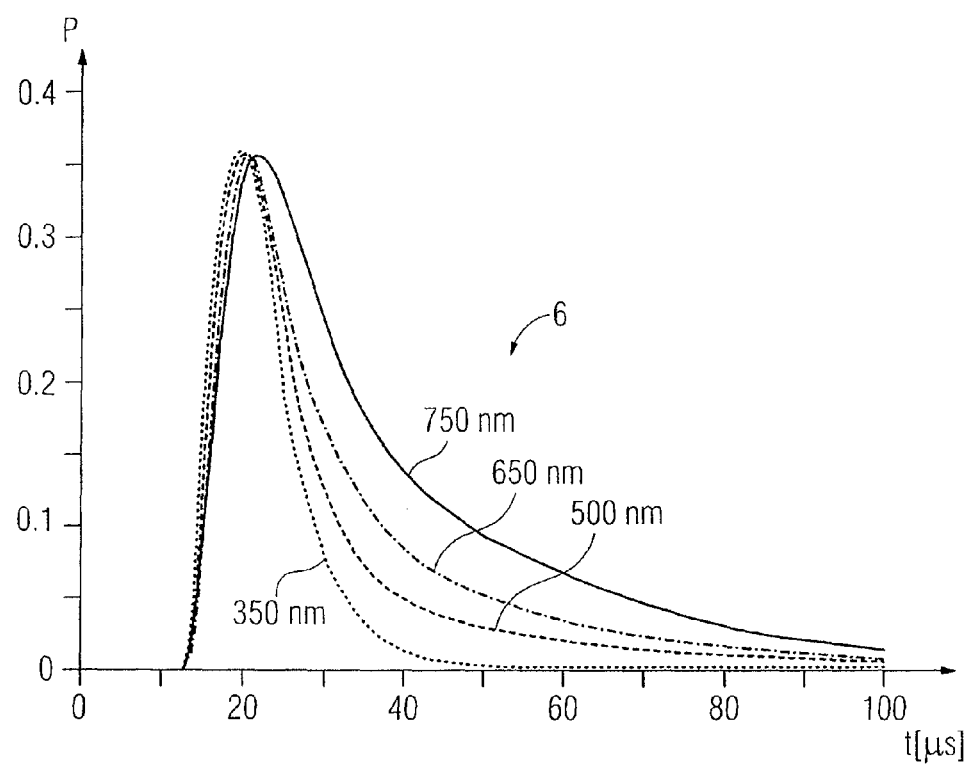
FIG. 2 shows a graphical plot of various spectral components of a xenon light flash.

FIG. 2 shows various spectral components of a xenon light flash 6 with their scaled output power P over the time t (taken from the above-mentioned technical information from Newport Corporation). The wavelength range of the light flash 6 extends from the infrared to the ultraviolet. The duration of the light flash 6 is shorter with respect to the short-wave components than in the case of the longer-wave components.

Wavelength-dependent absorption of the light flash 6 occurs as it is transmitted through the measuring cuvette 1 by the components of the measured gas 2, where many measured gas components of interest display very different absorption behavior.

Figure 3:
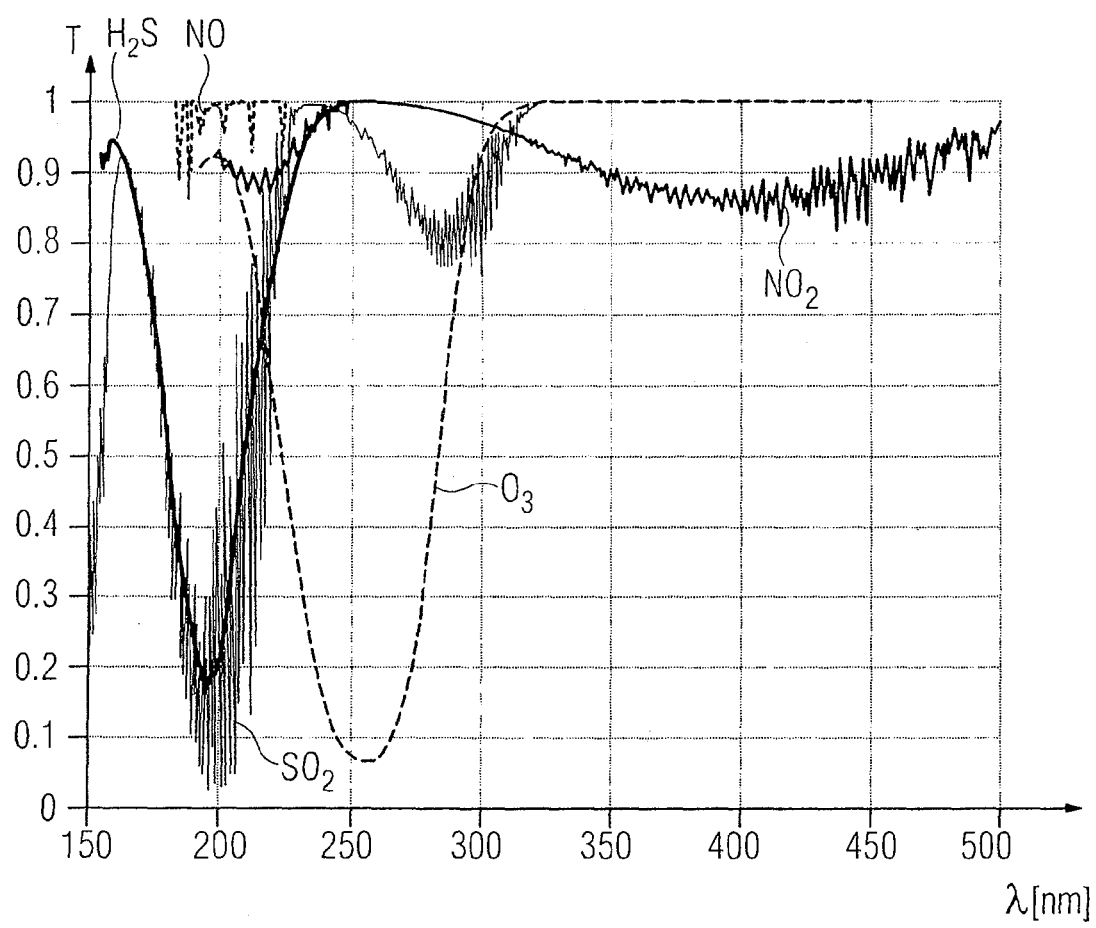
FIG. 3 shows a graphical plot of the UV transmission spectra of several selected gases.

FIG. 3 shows exemplary absorption behavior (transmission T over the wavelength λ) of the relevant gases $H_2S$, $NO_2$, $SO_2$, NO, and $O_3$ in environmental measuring technology in the ultraviolet range.

The detector 7 (FIG. 1) is selected so that it can detect the wavelengths of the respective observed wavelength range. For the above-mentioned gases, this is, e.g., the ultraviolet range. The detector 7 generates the detector signal 10 via the sum or the integral of the wavelengths; i.e., the detector 7 is non-selective. The detector 7 preferably detects the various wavelengths with more or less equal sensitivity. If the detector 7 is very broadband, interfering wavelength ranges outside the observed wavelength range can be masked out by an optical bandpass filter 12.

The emitted wavelength components vary over the duration of the light flash 6. As a result, the wavelength-dependent absorption by the measured gas components also varies, so that the time pulse curve of the light flash 9 incident on the detector 7 is different from the light flash 6 generated by the flash discharge lamp 4. The detected light flash 9 and therefore the detector signal 10 thus contain information about the absorption in the measuring cuvette 1. If the wavelength-specific absorption bands of the measured gas components are different, i.e., they do not overlap or only partially overlap, the detected light flash 9 and therefore the detector signal 10 also contain information about the concentrations of the individual measured gas components in the measured gas 2. In the analysis device 8, by analyzing the pulse curve of the detector signal 10 corresponding to the light flash 9 incident on the detector 7, the concentrations of selected measured gas components of interest are determined and output as the analysis result 11. In the case of multiple measured gas components to be quantitatively determined, chemometric analysis methods come into consideration, in particular multivariate statistical methods. From the above statements, it results that the detector 7 must allow a time resolution of the received light flash 9. A required time resolution in the microsecond range results from FIG. 2. This can be achieved by optopneumatic detectors, photodiodes, or photocells.

Figure 4:
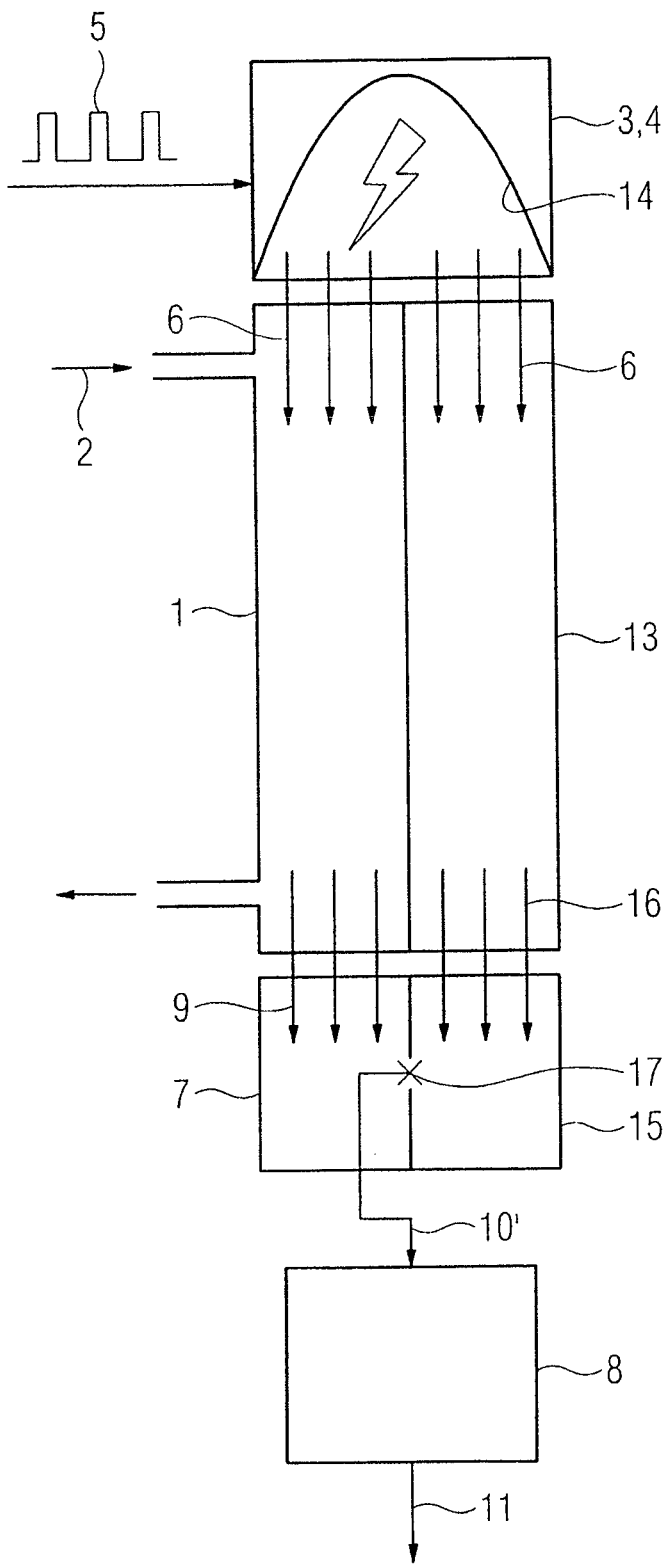
FIG. 4 shows a two-beam gas analyzer in accordance with an embodiment of the invention.

FIG. 4 shows a schematic illustration of a further exemplary embodiment of the gas analyzer according to the invention in a two-beam embodiment. Here, in addition to the measuring cuvette 1 having the measured gas 2 to be analyzed, a reference cuvette 13 is provided, which is filled with a reference or zero gas. The light 6 emitted by the light source 3 is portioned by a light distributor 14, in the form of a reflector here, onto the measuring cuvette 1 and the reference cuvette 13. A further detector 15 is arranged downstream from the reference cuvette 13 and the analysis device 8 analyzes the time difference pulse curve of the light flashes 9, 16 incident on the detectors 7, 15. In the present exemplary embodiment, the two detectors consist of two gas-filled receiver chambers having an interposed differential pressure sensor or flow sensor 17, which generates a detector signal 10' corresponding to the differential pulse shape of the light flashes 9, 16 incident on the detectors 7, 15.

Figure 5:
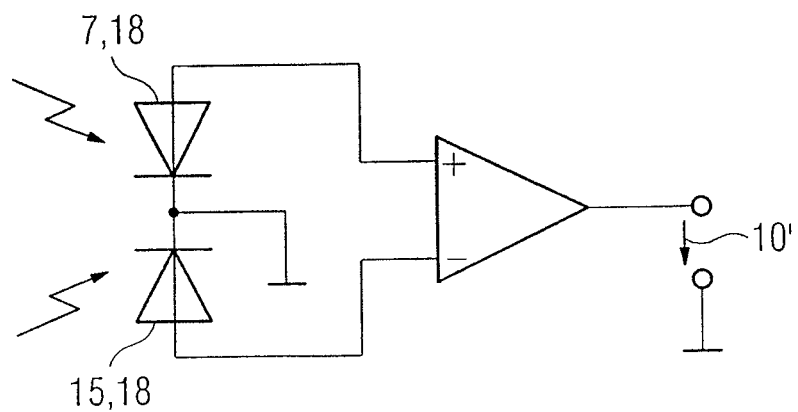
FIG. 5 shows a first circuit of two photodetectors for the two-beam gas analyzer in accordance with the invention.
Figure 6:
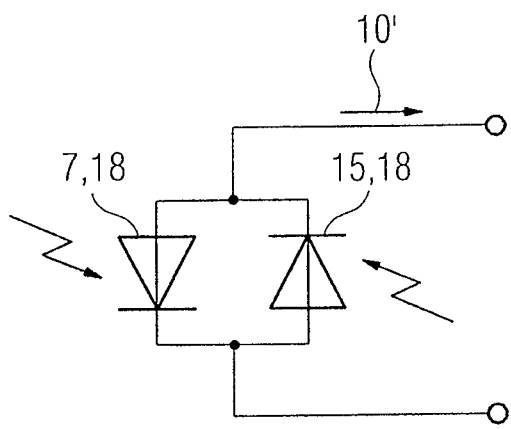
FIG. 6 shows a second circuit of two photodetectors for the two-beam gas analyzer in accordance with embodiments of the invention.

FIGS. 5 and 6 show two circuit examples known from EP 0 387 483 A1 having photodiodes 18 to implement the detectors 7 and 15.

While there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A non-dispersive gas analyser comprising:
   a light source comprising a flash discharge lamp;
   a non-selective detector;
   a measuring cuvette containing a measured gas to be analysed, light being incident through the measuring cuvette onto the non-selective detector; and
   an analysis device connected downstream of the non-selective detector and configured to analyse a shape over time of each individual pulse of light flashes from the flash discharge lamp which is incident onto the non-selective detector;
   wherein the analysis device is configured to analyse the time pulse curve for its frequency content, and wherein the analysis device is further configured to determine at least two different components of the measured gas by multivariate analysis of each individual pulse of the light flashes.

2. The non-dispersive gas analyser as claimed in claim 1, wherein the flash discharge lamp is a xenon flash lamp.

3. The non-dispersive gas analyser as claimed in claim 2, wherein the non-selective detector is a photodiode.

4. The non-dispersive gas analyser as claimed in claim 2, wherein the non-selective detector is a photocell.

5. The non-dispersive gas analyser as claimed in claim 2, wherein the non-selective detector is an optopneumatic receiver filled with a gas mixture of components to be measured.

6. The non-dispersive gas analyser as claimed in claim 1, wherein the non-selective detector is a photodiode.

7. The non-dispersive gas analyser as claimed in claim 1, wherein the non-selective detector is a photocell.

8. The non-dispersive gas analyser as claimed in claim 1, wherein the non-selective detector is an optopneumatic receiver filled with a gas mixture of components to be measured.

9. The non-dispersive gas analyser as claimed in claim 1, further comprising:
   a reference cuvette filled with a reference or zero gas;
   a further detector arranged downstream; and
   a light distributor which portions the light emitted by the light source onto the measuring cuvette and the reference cuvette;
   wherein the analysis device is further configured to analyse a differential pulse curve of the light flashes incident on the non-selective detector and the further detector.

* * * * *